US00PP08853P

United States Patent [19]

Buszard et al.

[11] Patent Number: Plant 8,853

[45] Date of Patent: Aug. 2, 1994

[54] JUNE-BEARING STRAWBERRY NAMED CHAMBLY

[75] Inventors: Deborah Buszard, Montreal West; Khanizadeh Shahrokh, Baie d'Urfé, both of Canada

[73] Assignee: McGill University, Montreal, Canada

[21] Appl. No.: 912,350

[22] Filed: Jul. 13, 1992

[51] Int. Cl.[5] ..... A01H 5/00

[52] U.S. Cl. ..... Plt./48

[58] Field of Search ..... Plt. 48

[56] References Cited

PUBLICATIONS

HortScience, Shahrokh et al., 1990, 25(8):984–985.

*Primary Examiner*—James R. Feyrer
*Assistant Examiner*—E. F. McElwain
*Attorney, Agent, or Firm*—Foley & Lardner

[57] ABSTRACT

A Nordic-type strawberry variety named "Chambly" combines the characteristics of cold-hardiness, adaptability to various soil conditions, vigor and strength, absence of suckering and its high yield of firm, deep red fruit with raised neck, elevated calyx and uniform well-colored flesh. Chambly yields strawberries characterized by an excellent taste (slightly sugary), a very fresh appearance and appealing texture, with a real strawberry aroma and no noticeable aftertaste.

6 Drawing Sheets

BACKGROUND OF THE INVENTION

The present invention relates to a new and distinctive cultivar of strawberry plant named Chambly. This cultivar belongs to the genus Fragaria, whose fruits are juicy edible and usually red, cultivated for culinary purposes.

Species of strawberry plants vary in color, size, shape, acidity, and other commercially important and botanically significant characteristics. Strawberries frequently bear flowers and fruit simultaneously, and fruit tends to ripen randomly on the stems.

ORIGIN OF THE VARIETY

The new cultivar of the present invention was developed in L'Acadie, Quebec from a cross between "Sparkle" and "Honeoye". "Sparkle", a previously popular commercial cultivar in eastern Canada, is noted for its high fruit flavor (Craig, D. L., 1979, Culture du fraisier dans l'est du Canada, Agriculture Canada, Publ. 1585). "Honeoye" is a high-yielding cultivar with large fruit size well-adapted to the northeast (Estabrooks and Luffman, 1989, Strawberry cultivar evaluatin in New Brunswick, Canada, Adv. Strawberry Production, 8: 58–61). "Chambly" has been tested at Agriculture Canada, L'Acadie, Québec, since 1984. L'Acadie is located 35 km south of Montreal (45°) at an elevation of about 46 m above seal level. Climate at L'Acadie is charactrerized by low temperatures in winter (below −25° C.), cool, humid conditions in spring, and warm, humid conditions (25° to 35° C., 70% relative humidity) in summer.

'Chambly' is a result of a cross between 'Sparkle'×'Honeoye'. The seed parent, 'Sparkle' was a product of 'Fairfax' (from 'Royal Sovereign'×'Howard 17')×'Aberdeen'. The pollen parent 'Honeoye' was a product of 'Vibrant' (from 'Sparkle'×'Valentine')×'Holiday' (from 'NY844'×'Raritan').

A new variety was originated from a cross made in a controlled breeding program in St-Jean-sur-Richelieu, Quebec. The straberry variety of the present invention, 'Chambly' was discovered and selected as a plant within the progeny of the stated cross in a controlled environment in St-Jean-sur-Richelieu, Quebec. Asexual reproduction of the new variety, as performed at St-Jean-sur- Richelieu in the greenhouse has demonstrated that the combination of characteristics as herein disclosed for the new variety are firmly fixed and are retained through successive generations of asexual reproduction.

This new cultivar can be asexually reproduced either by tip-cutting or tissue culturing. It can also be sexually reproduced such as by seed propagation.

DESCRPTION OF THE PRODUCTION

The accompanying photographs illustrate the color and other features of the new cultivar showing it in various stages of fruit maturation.

DESCRIPTION OF THE VARIETY

The cultivar of the present invention is the first June-bearing strawberry cultivar (*Fragaria*×*ananassa* Duch.) bred specifically for southern Québec conditions. This cultivar was released because of its high yields of firm, deep red fruit with raised neck, elevated calyx, and uniform well-colored flesh. Therefore, it is recommended for fresh market and processing.

Chambly adapts to various soils, but prefers neutral (approximately pH 6.8) to acid soil.

"Chambly" plants are of low vigor (Table 1), medium in size, with four to six inflorescences per plant, and can tolerate winter temperatures below −25° C. (with 10 cm of straw mulch cover).

TABLE 1

| Variables[x] | Ratings for fruit and plant characteristics of "Chambly" and standard strawberry cultivars.[z,y] | | | | | | |
|---|---|---|---|---|---|---|---|
| | Chambly | Bounty | Glooscap | Honeoye | Kent | Redcoat | Sparkle |
| Fruit color | 4.0 a | 3.3 b | 3.0 b | 3.0 b | 2.5 c | 3.0 b | 3.0 b |
| Interior fruit color | 4.0 a | 3.0 bc | 3.1 b | 3.0 bc | 2.5 cd | 2.8 bc | 2.0 d |
| Flavor | 3.7 a | 3.8 a | 3.1 b | 3.0 b | 3.0 b | 3.0 b | 3.6 a |
| Firmness | 3.8 a | 2.0 d | 2.6 cd | 3.0 bc | 3.3 ab | 2.8 bc | 2.0 d |
| Neck[w] | 4.0 a | 3.0 ab | 3.4 ab | 3.0 ab | 3.5 ab | 3.8 a | 2.4 b |
| Calyx[w] | 4.8 a | 4.0 a | 4.4 a | 2.0 c | 3.2 b | 3.0 b | 3.4 b |
| Ease of decapping | 1.8 c | 1.8 c | 1.3 c | 5.0 a | 4.0 ab | 3.6 b | 2.4 c |
| Achene position[w] | 3.0 a | 3.0 a | 2.0 a | 2.0 a | 2.3 a | 2.8 a | 2.3 a |
| Stolonization and vigor | 3.0 c | 4.0 abc | 4.0 abc | 3.3 bc | 4.2 ab | 4.3 ab | 4.7 a |
| Leaf disease symptoms | 4.4 a | 3.0 b | 4.0 a | 3.3 ab | 3.6 ab | 3.0 b | 3.0 b |

Figure 7:
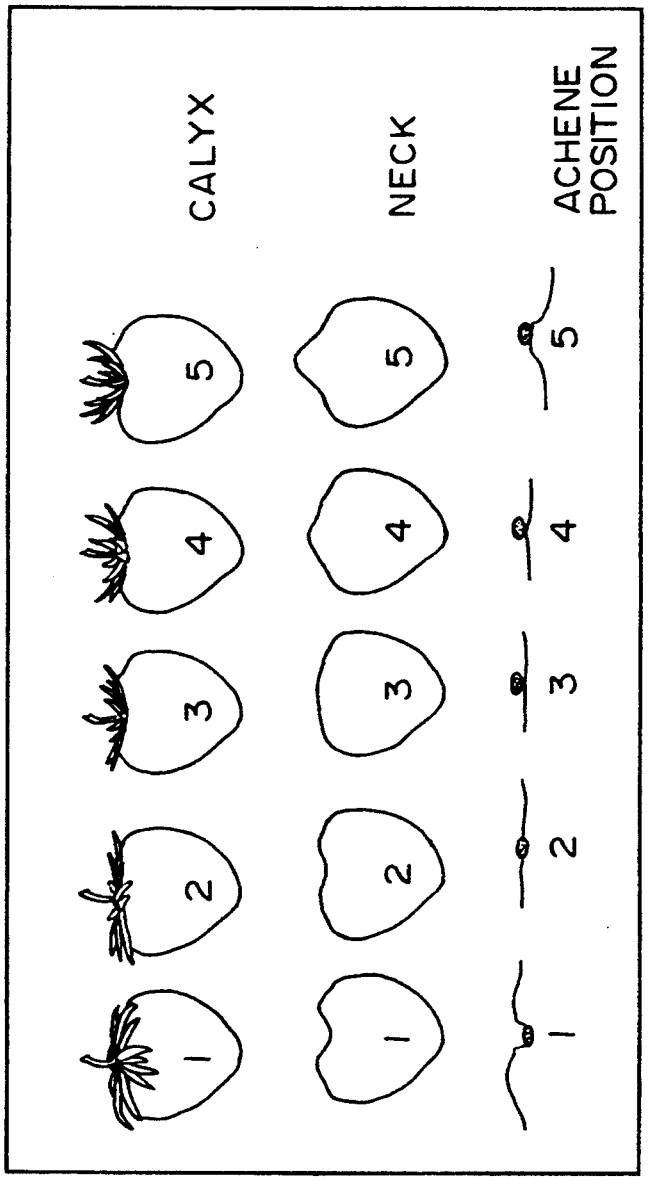
FIG. 7 shows the classification of strawberry fruit with respect to thier calyx, neck and achene position.

[z]Average of 2 years (1988–1989), using eight replicates except for flavor, which is the average of 22 determinations, data were transformed using an arcsin transformation prior to performing ANOVA.
[y]Mean separation within row by Duncan's new multiple range test, p = 0.05.
[x]Fruit color: 1 = pale, 5 = dark; interior fruit color; 1 = pale, 5 = dark; flavor: 1 = bad, 5 = good; firmness: 1 = soft, 5 = hard; decapping: 1 = easy, 5 = difficult; stolonization and vigor: 1 = weak, 5 = vigorous; leaf disease symptoms: 1 = entire leaf area affected, 5 = no symptoms.
[w]For description, see FIG. 7.

Prior to maturity, the fruit of the Chambly variety has a pink color. When fully ripe, the fruit has a reddish color identified with color 7.5R $\frac{3}{8}$ of the Munsell Book Colour Chart (Macbeth Division of Kollmorgen Corporation, 2441 N. Calvert Street, Baltimore, Md. 21218).

Figure 8:
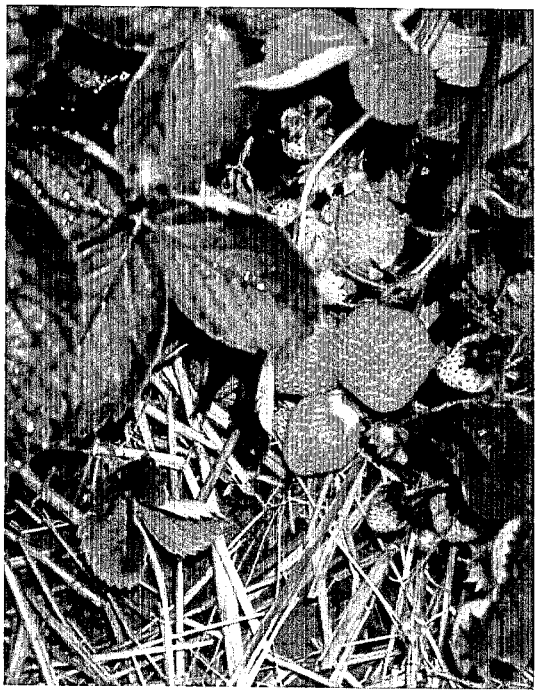
FIG. 8 is a view of fruits of the variety grown in a field and in different stages of maturity.

The prior-to-maturity strawberries shown in FIG. 8 have a dark pink color identified with color 7.5R 5/14 of the Munsell Book Colour Chart (MacBeth Division of Kollmorgen Corporation, 2441 N. Calvert Street, Baltimore, Md. 21218). When fully ripe (FIG. 9), the fruit has a reddish color identified with color 7.5R 4/14 of the Munsell Book Colour Chart.

Figure 2:
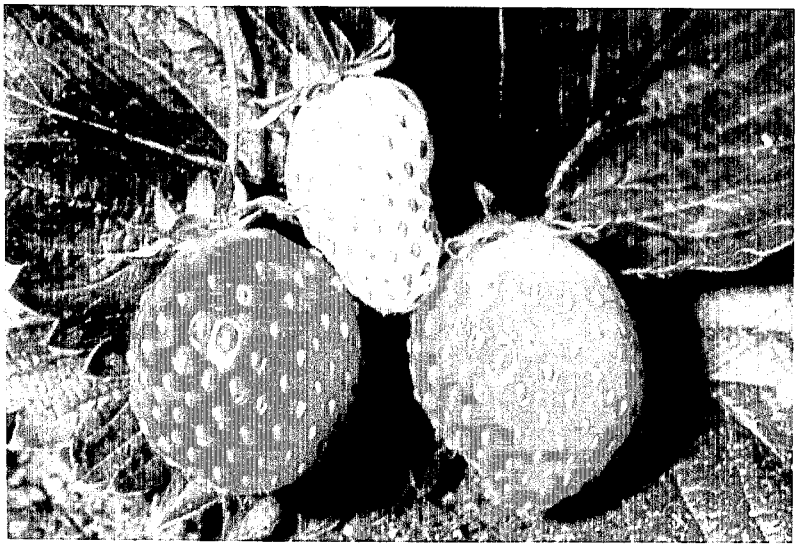
FIG. 2 is a close-up view of fruits of the variety in different stages of maturity.
Figure 3:
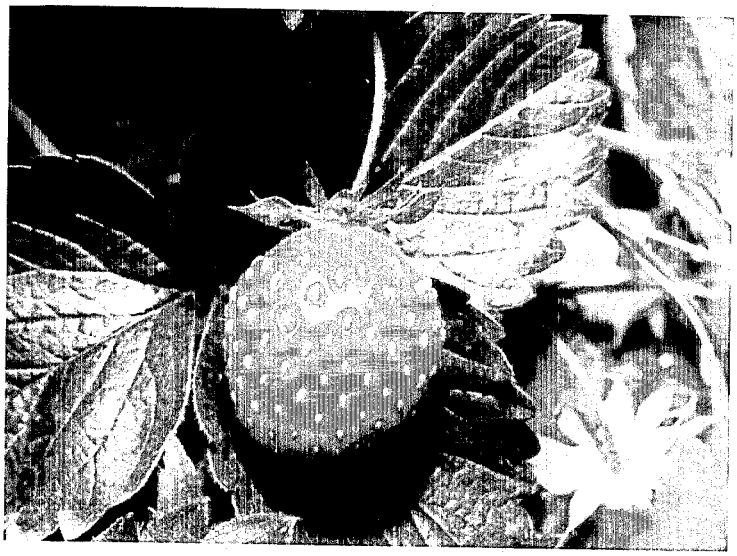
FIG. 3 is a close-up view of the mature fruit of the variety and, in addition, provides a good view of the leaves of the plant.
Figure 4:
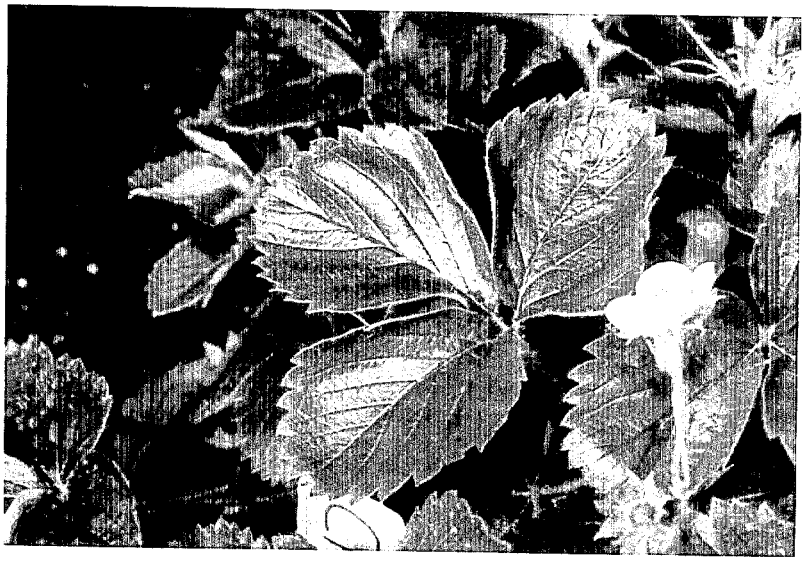
FIG. 4 is a close-up view of the leaves of the variety.
Figure 9:
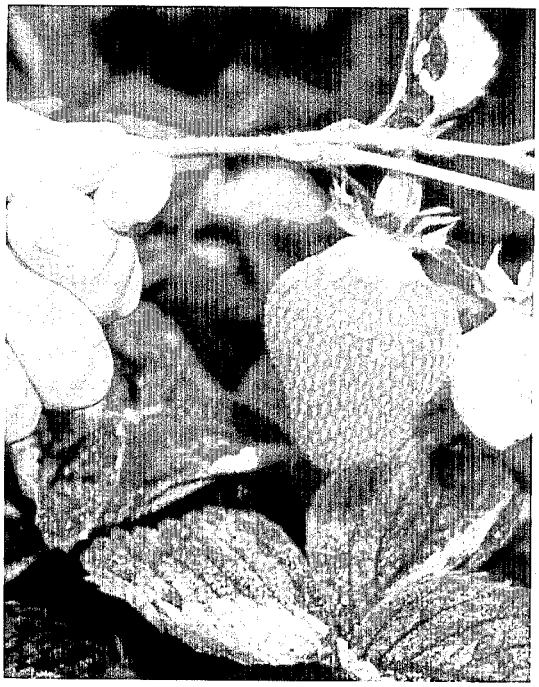
FIG. 9 is a close-up view of the mature fruit of the variety grown in a field.

Fruit shape is conic and the calyces are reflexed (FIG. 7 and 9; Table 1). Fruits are medium size (8 to 10 g) with a white, raised (2 to 3 mm) neck (FIGS. 2 and 3; Table 3). Skin is shiny and deep red at maturity, and the flesh is red throughout (FIG. 3, Table 2).

TABLE 2

| Cultivars | Comparison of the yield and average fruit size of "Chambly" with standard strawberry cultivars grown at L'Acadie, Québec.[z] | |
|---|---|---|
| | Yield (g/2-m row) | Fruit wt (g/fruit) |
| Chambly | 5970 a[y] | 8.9 a |
| Bounty | 4330 cd | 6.9 b |
| Glooscap | 5690 ab | 7.5 ab |
| Honeoye | 4940 bc | 9.1 a |
| Kent | 5630 ab | 8.9 a |
| Redcoat | 3470 c | 6.6 b |
| Sparkle | 3780 de | 6.5 b |

[z]Average of 3 years (1987–1989), using eight replicates.
[y]Mean separation within columns, by Duncan's new multiple range test, P = 0.05.

The leaves, when fully developed, have a dark green color, corresponding to color 7.5 GY $\frac{3}{4}$ of the Munsell Book Colour Chart and are three-lobed. Leaflets are slightly folded, medium size, obovate to spherical, with sharp serrations.

Figure 1:
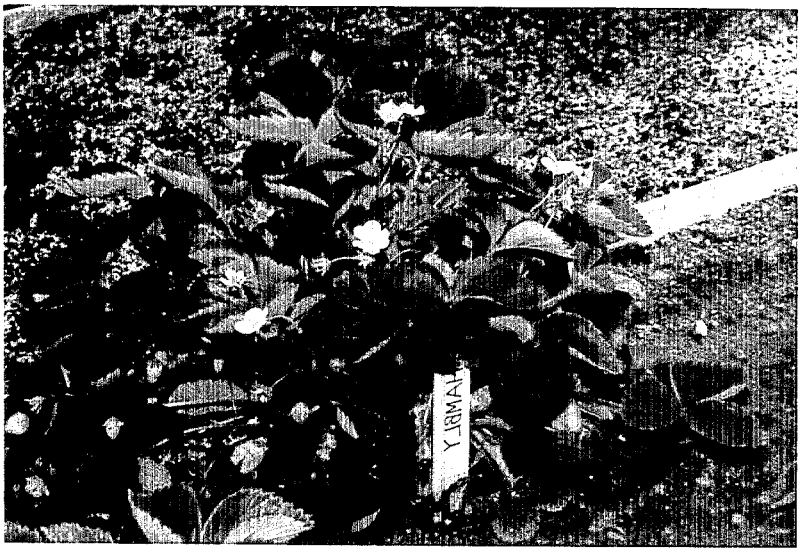
FIG. 1 is a view of a strawberry plant of the Chambly variety, showing the fruit in different stages of maturity.

Petioles are moderately long and slightly drooping. Plants have a sparse appearance and have an average height lower than other strawberry plant variety (FIG. 1). The "Chambly" strawberry plant of the present invention has an average height of about 9 inches and an average width of about 20 inches, whereas the "Oka" strawberry plant has an average height of about 10 inches and an average width of about 24 inches. The lower the strawberry plant is, the more the fruits are exposed to sunrays which accelerates the maturity process of the fruit.

The plant stems are hairy and have yellow/green color corresponding to color 5GY 6/8 of the Munsell Book Colour Chart.

The plants showns in the appended FIGS. 1 to 6 have been grown in a greenhouse with clear glass windows with a sun filter curtain which blocks 60% of the sunrays (Cravo Equipment Ltd., Brantford, Ontario, Canada N3T 5L4). The plants have been grown with a sixteen (16) hour photoperiod/day. Sodium high presure lamp of 400 W are used when the intensity of the sunrays is too low. The temperature inside the greenhouse was 20° C. with 50% RH (relative humidity). It should be appreciated that "Chambly" fruits from "Chambly" plants grown outside are bigger and of more reddish color than the fruits matured in a greenhouse.

The color evaluations described in FIGS. 1 to 6 were made in St-Jean, Québec, Canada, on the morning of Mar. 13, 1992, at 11:45 AM in a greenhouse. Viewing was effected in filtered sunlight through a 60% sunblock curtain (Cravo Equipment Ltd.), under dry cool conditions of a cloudy day with good visibility and a temperature of about −12° C.

Figure 10:
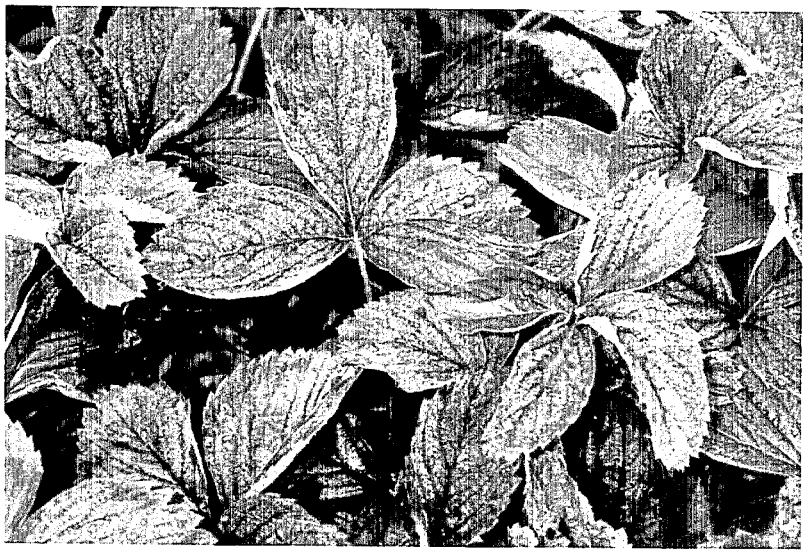
FIG. 10 is a close-up view of the leaves of the variety grown in a field.

The color evaluations described in FIGS. 8 to 10 were made in Lavaltrie, Québec, Canada, on the morning of Jul. 7, 1992, at 9:30 AM in a strawberry field. Viewing was effected in direct sunlight under dry cool conditions of a cloudy day with good visibility and a temperature of about 60° F.

As shown in Table 3 below chemical analyses revealed substantial differences between "Chambly" and typical cultivated strawberry varieties. These analyses involved comparisons of pH, Brix value (percent of soluble solids), acidity (percent of citric acid found in the strawberries) and humitidy (percent of moisture).

TABLE 3

| | ph | Brix value | Acidity (%) citric acid | Humidity |
|---|---|---|---|---|
| Chambly variety | 3.24 | 8.3 | 58 | 76.16 |
| Typical cultivated | 3.15 | 8.4 | 55 | 78.2 |

One of the major soluble components of strawberries and other soft fruit is its sugar. The sugar-to-acid ratio is important in determining flavor and commercial acceptability. Sensory evaluations indicated that Chambly yields berries were characterized by an excellent taste (slightly sugary). Fruit flavor (sweetness) is similar to that of "Bounty" and "Sparkle" (Table 1). There is no noticeable aftertaste, and the fruits has real strawberry aroma. It has also a very fresh appearnace and appealing texture.

Fruits are firm, similar to "Kent", and can be decapped as easily as "Glooscap". The calyx does not separate from the fruit at harvest time. Percent juice lost after thawing did not differ significantly (P=0.05, n=8) among cultivars and ranged from 42% to 53%. "Chambly" has outyielded "Bouty", "Honeoye", "Redcoat", and "Sparkle" in our trials (Table 2). Plants are partially tolerant of the herbicide terbacil [5-chloro-3-(1,1-dimethylethyl)-6-methyl-2,4(1H, 3H)pyrimidine-dione]. No symptoms of powdery mildew (*Sphaerotheca macularis* Walls ex Fr.), leaf scorch (*Diplocarpon carlina* Ell. and Ev.), or leaf blight (*Dendrophoma obscurans* Ell. and Ev.) were observed during the course of its evaluation (Table 2).

Figure 5:
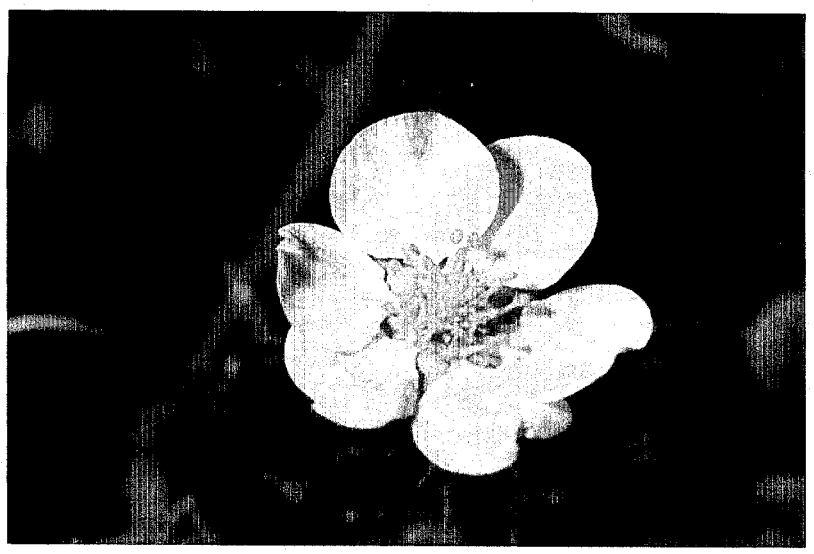
FIG. 5 is a close-up view of the flowers of the variety.
Figure 6:
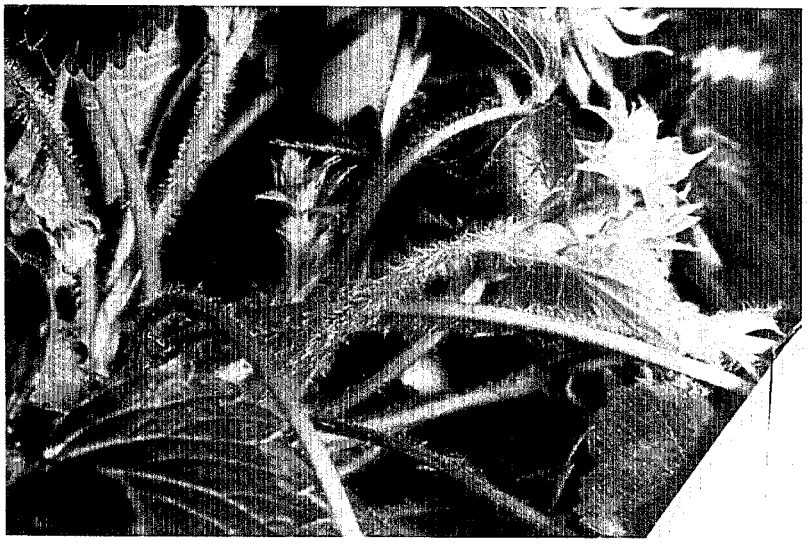
FIG. 6 is a view of the velvet stem of the variety.

Inflorescences are held erect on long, moderately thick peduncles during bloom, becoming arched (semi-erect) as the fruit mature. Inflorescences generally have 10 to 20 flowers (FIG. 5).

Inflorescences of Chambly are produced from June until September in northern temperate climates. Fruits ripen from June to late September in this zone.

The variety should be planted in sunny and dry locations spaced about 10 inches apart. Chambly is useful for home gardens, as well as "pick-your-own" and contract growing. After harvesting, all twigs that produced fruit, i.e., those that are two years old, should be pruned. In addition, side branches should be pruned on one year-old twigs.

The strawberry variety of the present invention, 'Chambly', requires a short day length of less than 10 hours and low temperature (>0° C. for at least 45 days) to induce flowering.

Table 4 compares the flavor and texture attributes of the 'Chambly' cultivar with six other strawberry cultivars.

TABLE 4

| | FLAVOR[z] | | | | | | |
|---|---|---|---|---|---|---|---|
| Cultivar | Strawberry | Sweetness | Astringency | Honey | Melon | Bitterness | Acidity |
| Bounty | 10.4a | 13.2a | 5.4b | 11.4a | 10.6a | 6.2cc | 4.5c |
| Chambly | 7.1bc | 8.2bc | 8.4a | 8.7bc | 8.5ab | 8.8a | 6.4bc |
| Glooscap | 8.2bc | 8.6b | 6.9ab | 9.1b | 8.0b | 8.4ab | 7.5ab |
| Kent | 9.0ab | 6.9bc | 7.7a | 7.0cd | 7.4b | 6.6bc | 8.9a |
| Midway | 6.5c | 6.9bc | 8.9a | 6.8cd | 7.6b | 8.5ab | 8.7a |
| Oka | 6.8c | 6.4c | 8.5a | 6.2d | 6.6b | 8.0abc | 8.9a |
| LSD[x] | 2.1 | 2.0 | 2.1 | 2.1 | 2.1 | 2.1 | 2.0 |

| TEXTURE[y] | |
|---|---|
| Juiciness | Firmness |
| 8.7abc | 7.4b |
| 9.5ab | 8.8a |
| 7.0c | 7.4b |
| 4.8d | 8.4a |
| 10.1a | 4.2c |
| 8.0bc | 6.7b |
| 2.0 | 0.9 |

[z]Each value is the total rank of at least 40 determinations.
[y]See FIG. 1 for details of scaling.
[x]Least significant difference at 5% level.

The line scale used to evaluate flavour and texture, skin colour, brightness, seediness and flesh colour is set forth in Table 5 below.

TABLE 5

| Variable | Line Scale | |
|---|---|---|
| Flavour | 15 cm | |
| Strawberry flavour | none | strong |
| Sweetness | none | very |
| Astringency | none | strong |
| Honey flavour | none | strong |
| Melon flavour | none | strong |
| Bitterness | none | very |
| Acidity | none | very |
| Texture | 15 cm | |
| Juiciness | none | very |
| Firmness | soft | very firm |
| Appearance | 15 cm | |
| Skin colour | light red | dark red |
| Brightness | none | very |
| Seediness | not seedy | very seedy |
| Flesh colour | light red | dark red |

Susceptibility of the Chambly cultivar to red stele (*Phytophthora fragariae* Hickman) is not known and further experiments are needed to determine the degree of resistance to different races of *P. fragariae*.

We claim:

1. A new and distinct cultivar of *Fragaria*×*ananassa*, named Chambly, as herein shown and described, characterized particularly as to uniqueness by the combined characteristics of cold-hardiness, adaptability to various soil conditions, vigor and strength, absence of suckering and its high yield of firm, deep red fruit with raised neck, elevated calyx and uniform well-colored flesh.

* * * * *